United States Patent [19]

Yamazaki et al.

[11] 3,945,181

[45] Mar. 23, 1976

[54] PROCESS AND APPARATUS FOR MEASURING UNIFORMITY OF PHYSICAL PROPERTIES OF YARN

[75] Inventors: Chikayasu Yamazaki, Kyoto; Takao Nakayama; Noriyuki Kawabe, both of Otsu, all of Japan

[73] Assignee: Toray Industries, Inc., Tokyo, Japan

[22] Filed: Apr. 25, 1974

[21] Appl. No.: 463,890

[30] Foreign Application Priority Data

Aug. 11, 1973 Japan .............................. 48-124943
Aug. 11, 1973 Japan .............................. 48-124944

[52] U.S. Cl. .................................... 57/34 R; 73/160
[51] Int. Cl.$^2$ ..................... D01H 13/32; D01H 13/26; D01H 13/14; G01N 21/00
[58] Field of Search ....... 57/1 R, 34 R, 106; 73/160, 73/95.5; 118/8–11; 427/8–10; 68/13 R

[56] References Cited

UNITED STATES PATENTS

| | | | |
|---|---|---|---|
| 2,209,584 | 7/1940 | Somerville | 57/59 X |
| 3,303,698 | 2/1967 | Loepfe | 73/160 |
| 3,405,556 | 10/1968 | Gonsalves et al. | 73/160 |
| 3,465,550 | 9/1969 | Strom et al. | 68/13 R |
| 3,471,702 | 10/1969 | VanVeld | 73/160 X |
| 3,613,347 | 10/1971 | Carruthers | 57/34 R X |
| 3,660,972 | 5/1972 | Neill | 57/34 R |
| 3,667,292 | 6/1972 | Hada | 57/34 R X |
| 3,680,298 | 8/1972 | Saunders | 57/34 R |
| 3,680,299 | 8/1972 | Lee | 57/34 R |
| 3,773,548 | 11/1973 | Baker et al. | 427/10 |
| 3,885,232 | 5/1975 | Goto | 73/160 X |

*Primary Examiner*—Donald E. Watkins

[57] ABSTRACT

Yarn is continuously supplied to a measuring system with an applied twist of at least 100 turns per meter. A beam having a continuous spectrum from the visible region to the near-infrared region is impinged upon the yarn and measurements are taken on the beams reflected from the yarn. The refected beams are divided into two parts. The characteristics of the near-infrared region are applied to one part, and luminosity characteristics are applied to the other. The ratio of intensity of the former to that of the latter is determined. This ratio corresponds to the uniformity of physical characteristics in the direction of the length of the yarn.

14 Claims, 4 Drawing Figures

1
2
YM
3A
3B
3C
3D
4
5
6
7
8
9
10
11
12
13A
13B
14A
14B
15A
15B
16
17
45°
45°
E1
E2
E1'
E2'

B
B
B
B
TIME
MEASURED VALUE

A
B
1.0
0.5
0
0
50
100
150
MEAN VALUE OF APPARENT FLUCTUATION (%)
IMPARTED TWIST (TURNS/METER)

17
19
ΔY
YM
YS
18M
16
E1M
E2M
15A
15B
14A
14B
13A
13B
10
11
12
M
S
E1S
E2S
18S

PROCESS AND APPARATUS FOR MEASURING UNIFORMITY OF PHYSICAL PROPERTIES OF YARN

BRIEF SUMMARY OF THE INVENTION

The present invention relates to a process and apparatus for measuring uniformity of physical properties of yarn, and to promptly and precisely measuring uniformity in production or processing steps in the direction of the length of the yarn.

The physical properties of yarn vary even though it is produced continuously from the same material unless many operating conditions are carefully kept constant. However, in order to maintain these conditions strictly, very complicated and expensive means are required, even with all the advanced technology available at present. Even then, it is not practical or even possible to obtain perfect uniformity and a predetermined fluctuation range is established. Accordingly, the physical properties of yarn are controlled so that they normally vary within this range.

When this variation of physical properties of yarn is considered with reference to drawing of synthetic filaments, fluctuation of conditions such as draw ratio and drawing or cooling temperatures greatly affects the physical properties of the drawn yarn, such as the degree of molecular orientation, tensile strength, hooking strength, knotting strength, coefficient of expansion and modulus of elasticity, for example.

However, there are many causes of such fluctuation of physical properties, and it is nearly impossible to analyze each as it occurs. Further, such analysis is usually unnecessary, because the yarn product is graded on the basis of its final physical properties.

This determination of the physical properties of yarn may be carried out by measuring the degree of unevenness with which it accepts dye. Variations of physical properties correspond well to variations of dye unevenness.

The physical properties of interest in this determination are those possessed by the yarn product per se, the individual physical properties in the individual steps of the yarn producing process, for example, degree of molecular orientation in the drawing step.

Measurement of dye unevenness of yarn is carried out by visual observation, by a skilled worker, of fabric obtained by weaving or knitting these yarns, and the yarn is graded and classified as first grade, second grade or below standard.

However, knitting or weaving for the sole purpose of yarn inspection is not only complicated, but also requires many hours to provide the results. Also, because the measurement per se depends upon human preceptions of luminosity, subjective human factors intervene and the results vary in reliability depending upon human observation.

According to the present invention the defects of conventional measuring technologies are eliminated. The invention comprises:

1. applying a twist of at least 100 turns per meter to yarn continuously supplied to the measuring system,

2. impinging on the yarn a beam having a spectrum which is continuous from the visible region to the near-infrared region, and

3. dividing the beams reflected from the twisted yarn into two parts, imparting the characteristics of the near-infrared region to one of these parts and imparting luminosity characteristics to the other part, and sensing the ratio of the intensity of the former to the intensity of the latter.

DRAWINGS

Figure 1:
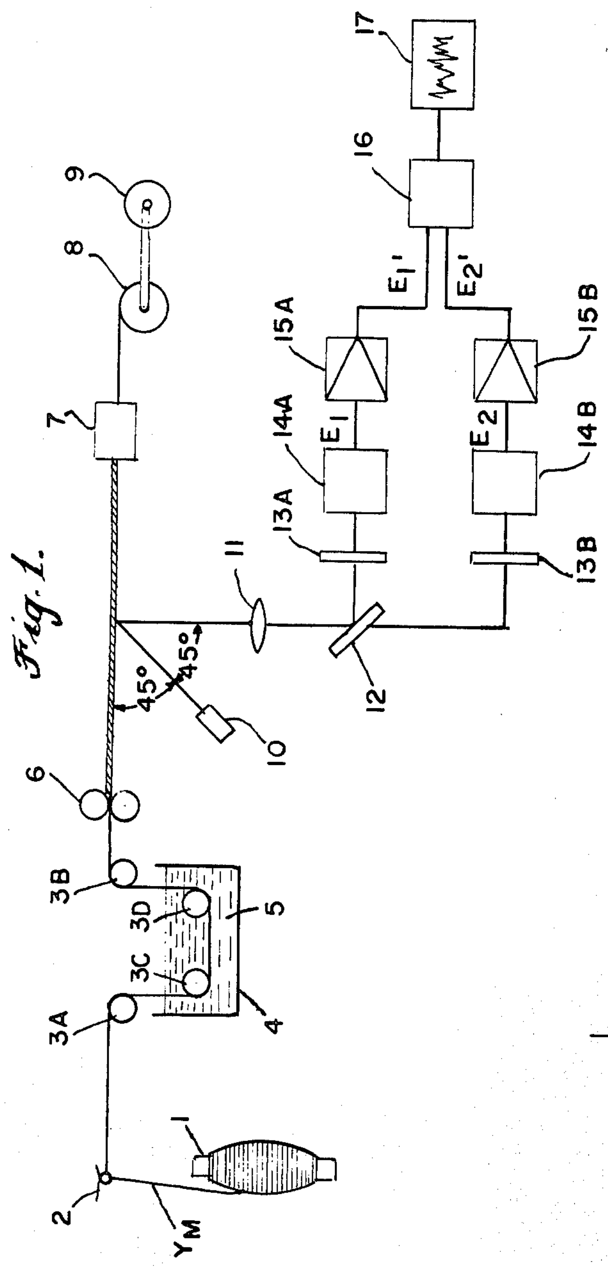
FIG. 1 is a schematic representation of one example of the present invention.

In the specification which follows, specific terms will be used to describe specific parts and features that are illustrated in the drawings. These are intended to be exemplary rather than limiting; the scope of the invention is not intended to be limited other than as defined in the appended claims.

DETAILED DESCRIPTION OF THE INVENTION

In FIG. 1, 1 is a bobbin carrying the yarn to be measured. 2 is a yarn take-out guide, 3A and 3B are yarn guide rollers, 4 is a dye bath which contains liquid dye 5, 6 is a pair of nip rollers, 7 is a false twist machine, conveniently of the spindle type, 8 is a yarn winding bobbin, 9 is a motor for driving bobbin 9, 10 is an incandescent lamp, 11 is a lens, 12 is a half mirror, 13A is a luminosity filter, 13B is a near-infrared interference filter, 14A and 14B are photoelectricity converters, 15A and 15B are voltage amplifiers, 16 is a logarithmic calculator and 17 is an analogue recorder.

Yarn ($Y_M$) from bobbin 1 is guided by yarn take-out guide 2 and guide rollers 3A – 3B, passed through said dye liquid and dyed. The dyed yarn ($Y_M$) is false twisted by false twister 7 and wound up on bobbin 8.

A light beam is directed by incandescent lamp 10, at an angle of 45° upon the false twisted yarn ($Y_M$). The reflected beams are directed at an angle of 45° of the initial beam, or 90° relative to the yarn, introduced to the half mirror 12 by lens 11. The half mirror 12 converts the reflected ray into two parts.

One such part is passed through luminosity filter 13A which has the same characteristics as those observed by the human eye and the other part of the reflected beam is passed through filter 13B having a peak in the near-infrared region (750 – 1200 m$\mu$). The intensities of the resulting beams are converted to electrical signals (voltage signals) $E_1$, $E_2$ which are amplified to conveniently high voltages by voltage amplifiers 15A, 15B, and such voltages are fed as $E_1'$, $E_2'$ into the logarithmic calculator 16.

By the logarithmic calculator 16 the logarithm of the ratio of the amplified electric signals (namely, log $E_1'/E_2'$) is determined and the result is continuously recorded and charted by the analogue recorder 17. This recorded value corresponds to the dye unevenness of the yarn in the direction of its length, which is equivalent to variations of physical properties in the direction of length of the yarn.

A further detailed explanation will be made with reference to the following example.

In this example, the logarithmic calculator 16 is used and the logarithm of the ratio of the two electric signals is determined. There are good reasons for adopting such means.

One reason is that, by using the ratio of the voltage signals, the influence of fluctuations of the source beam is minimized. The influence of change of shape of the yarn exerted is also minimized. When the intensity of the light beam source varies, the intensity of the reflected beam varies even if there is no dye unevenness in the yarn. Therefore, the measured result suggests dye unevenness even when no real dye unevenness exists. However, using divided reflected beams according to this invention, the divided beams fluctuate at the same ratio and therefore, the measured ratio is not affected at all.

Another reason is that, by carrying out logarithmic calculations, even a small input signal may be taken out as a large output signal.

However, even when treating the signals as heretofore described, when yarn shape fluctuates greatly during measurement, the measuring means cannot be called entirely sufficient for all purposes. Depending upon the shape of yarn, the light beam reflects in unexpected directions and sometimes the photoelectric converter cannot catch the reflected beam at all; even if the reflected beam is caught, it is likely to be very feeble, and it is necessary to use a high sensitivity photoelectric converter or voltage amplifier. In general, the higher the sensitivity of the photoelectric converter or voltage amplifier, the more expensive it becomes. Also, high sensitivity photoelectric converters or voltage amplifiers tend to be affected by various disturbances and to provide a low signal-to-noise ratio.

When twist is applied to the yarn this limits the fluctuation of its shape. When the dyeing conditions are uniform, reflected beams of the same intensity are always obtained. Further, the direction of the reflected beams becomes constant.

The relationship between the number of turns of twist and the measured value is of importance, as will now be discussed.

Figure 2:
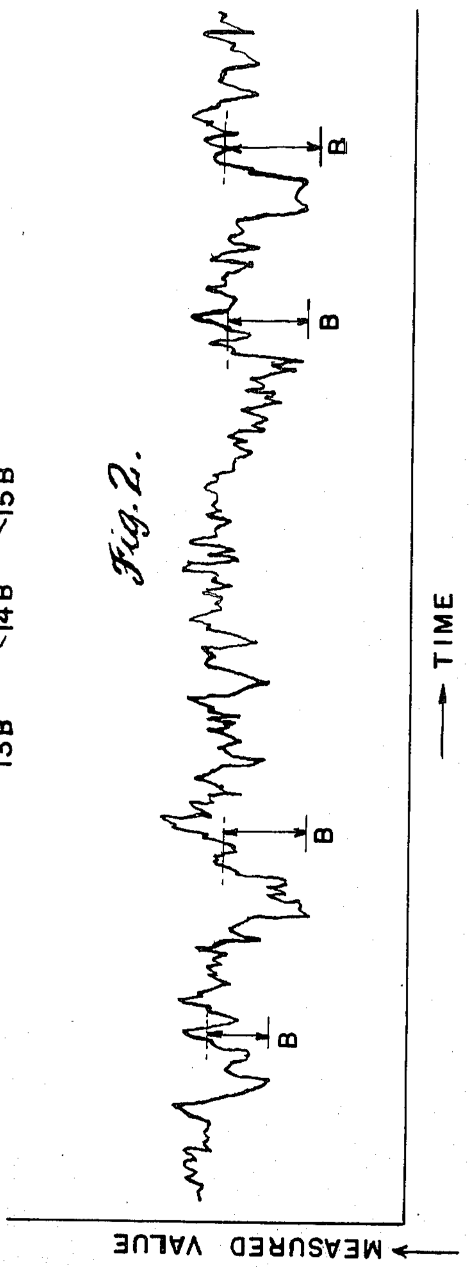
FIGS. 2 and 3 are graphs showing the relationship between change of shape of the yarn and measured values.

FIG. 2 illustrates measurements of dye unevenness of twisted yarn having a twist of 10 – 20 turns per meter (even yarn not positively twisted has this much twist) using the apparatus of FIG. 1. However, the yarn is not subjected to false twisting. The yarn used in this measurement is polyester yarn (75D, 36F, number of turns 20/M).

As will be apparent from FIG. 2, the measured value greatly fluctuates at points B. These fluctuations are not brought about by actual dye unevenness (hereinafter referred to as "apparent fluctuation") and this is confirmed by other measurements.

This apparent fluctuation is caused by development of stagnant twist, and by intermittent surging of twist. When such low twist as mentioned above is passed through a guide and a tension controlling device, friction developed by the guide and the tension device cause the twist to concentrate at one place. Such phenomenon is usually called "stagnant twist". When the torque due to twisting becomes larger than the friction forces, a surge of twist temporarily flows in the direction of length of the yarn, and the shape of the yarn at the point of measurement fluctuates wildly.

Figure 3:
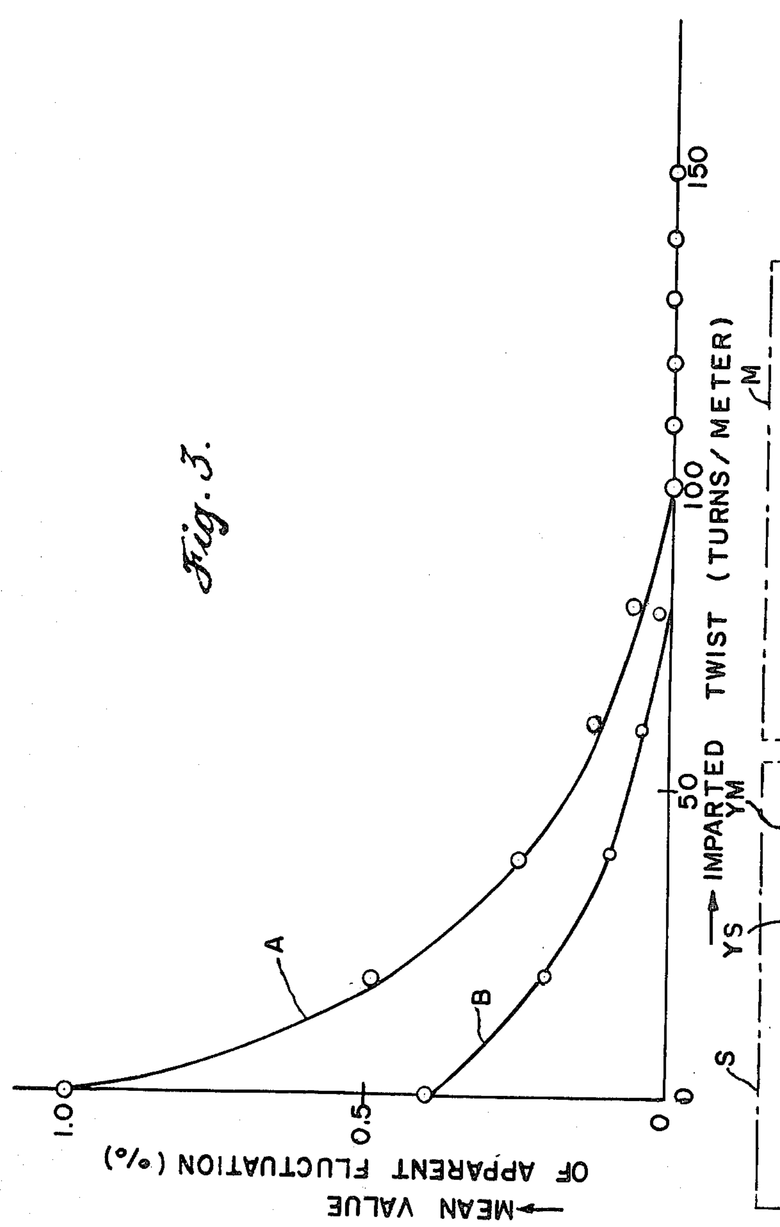

FIG. 3 illustrates measurements showing how the apparent fluctuation changes, using the apparatus of the example shown in FIG. 1. The yarns used in these measurements were polyester yarns (75D, 36F, number of turns 20 T/M), and bulky yarn obtained by processing such polyester yarn.

As will be apparent from FIG. 3, in both polyester yarn (curve A) and processed yarn (curve B), it is possible to prevent said apparent fluctuation by applying a twist of about 100 turns per meter. This phenomenon applies to almost all other yarns, as confirmed by experiments. This fact indicates that when a twist of at least 100 turns per meter is applied to the yarn, it is possible to curb the stagnant twist and the twist surging within ranges not affecting the measurements.

Next, the respective components of the apparatus shown in FIG. 1 will be explained in more detail.

Concerning the yarn supply system (namely, from bobbin 1 to the nip rollers 6), various modifications may be made. For example, when measuring already dyed yarn, it is unnecessary to provide the dye bath. It is also possible to supply yarn from a plurality of bobbins wound with yarns of different types by switching the bobbins successively, or such bobbins may be interconnected in advance.

Any conventional false twisting machine 7 may be used, including spindle type and pin type false twist machines. The ring traveler type, flyer type and uptwist type false twist machines may be used also, but they tend to be complicated and unwieldy.

Various forms of light beam may be used; the beam should have a visible region and a near-infrared region (wave length within the range of about 200 – 1200 m$\mu$). Also, the beam should have a continuous spectrum which is necessary to impart the needed luminosity characteristics to one of the divided reflected beams. The continuous near-infrared region is necessary to impart the near-infrared characteristics to the other divided reflected beam.

The incidence angle of the impinging beam and the angle of the reflected beam are not limited. However, the angles shown in FIG. 1 are convenient when the structure is made as illustrated, because of convenience in establishment of beam 10, of uniting the optical axes of the reflected beams, and of positioning the lens 11, half mirror 12, filters 13A and 13B and photoelectric converters 14A and 14B.

The direction of the light beam is not limited to the direction of movement of the yarn (i.e. along the length of the yarn), but it may be, for example, perpendicular to the running direction.

Regarding the photoelectric converters 14A, 14B, they are selected by taking into account the wave length of the impinging beam or its intensity. They may be photomultipliers or solar batteries.

When the intensity of the beam source is designated $I_0$ and the distribution of the intensity of the wave length of said beam is called $P_0(\eta)$, the following equation applies:

$$I_0 \int_{\eta_1}^{\eta_2} = P_0(\eta)d\eta, \tag{1}$$

where $\eta$ indicates wave length and $\eta_1$, $\eta_2$ indicate measured regions of the wave length.

Next, when the ratio of change of the amount of reflected beam according to the shape of yarn (shape coefficient) is called S and the distribution of the intensity of the reflected beam selectively absorbed by the yarn is called $P(\eta)$, the amounts of the beam permeating and reflecting the half mirror $I_{H1}$, $I_{H2}$ are expressed by the following two equations:

$$I_{H1} = C_1SP(\eta) \tag{2}$$

$$I_{H2} = C_2SP(\eta), \tag{3}$$

where $C_1$ designates the permeation ratio of the half mirror, and $C_2$ designates the reflection ratio of the half mirror.

Next, the intensity of the beam $I_1$ permeating the filter 13A and the intensity of the beam $I_2$ permeating the filter 13B are expressed by the following equations:

$$I_1 = C_1S \int_{\eta_1}^{\eta_2} P(\eta)\,\bar{y}_1(\eta)d\eta = k_1SI_0Y \quad (4)$$

$$I_2 = C_2S \int_{\eta_1}^{\eta_2} P(\eta)\,\bar{y}_2(\eta)d\eta = k_2SI_0, \quad (5)$$

where Y designates the Y value (brightness), $\bar{y}_1(\eta)$ designates the wave length characteristics of the filter 13A, $\bar{y}_2(\eta)$ designates the wave length characteristics of the filter 13B, and $k_1$ and $k_2$ are constants.

Accordingly, the ratio $\rho$ of $I_1$ to $I_2$ is $$= \frac{I_1}{I_2} = \frac{k_1SI_0Y}{k_2SI_0} = KY, \quad (6)$$

where K is a constant.

Although in general the brightness of a reflected beam is expressed as a brightness value L which is more in accord with the psychological sense than said Y value, it has been confirmed that this L value has a definite relation to said Y value, as expressed by the following equation:

$$L=100\sqrt{Y} \quad (7)$$

When the reflected beam from the yarn is divided and the characteristics of the wave length are imparted to each reflected beam, this makes it possible to measure the brightness value Y. Further, it is simple to cause this value to correspond to the aforementioned L value.

Now, even by such example, it is difficult to make up for measurement differences that occur in dyeing conditions as time goes by due to changes.

For example, the concentration of the dye liquid in the dye bath usually changes as time goes by. It is necessary to compensate the measured difference accordingly.

Figure 4:
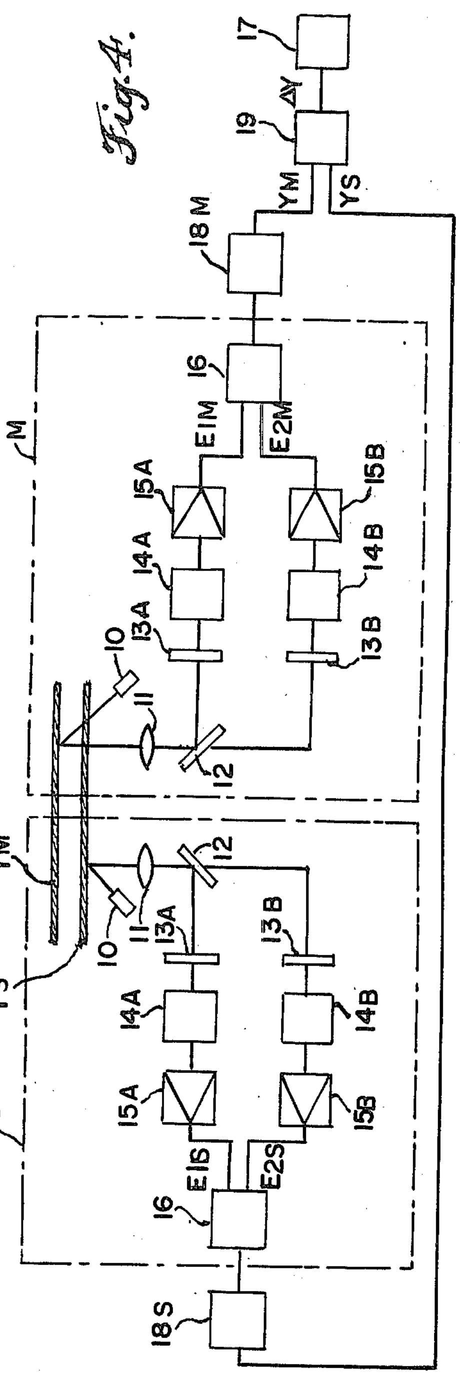
FIG. 4 is a schematic view showing another example of the invention.

FIG. 4 shows a means that is advantageous. In FIG. 4, like parts are similarly numbered and the yarn supply means and the yarn winding means are omitted.

FIG. 4 shows a simultaneous and continuous supply of yarn to be measured ($Y_M$) and also a standard yarn ($Y_S$). Measuring systems M, S like those shown in FIG. 1 are provided. The outputs of the respective measuring systems M, S (i.e. outputs of the logarithmic calculator 16) are introduced into integrators $18_M$, $18_S$ connected to the respective measuring systems M, S and the outputs of the integrators $18_M$, $18_S$ are introduced into a subtractor 19 and subtracted.

There is good reason why the measured difference due to change of dyeing conditions as time goes by may be compensated for by such structure.

When each signal is determined as shown in FIG. 4, the following equations apply:

$$Y_M = K_1 \int_o^T \log \left(\frac{E_{1M}}{E_{2M}}\right) \frown dt \quad (8)$$

$$Y_S = K_1 \int_o^T \log \left(\frac{E_{1S}}{E_{2S}}\right) \frown dt, \quad (9)$$

where $K_1$ is a constant and T is the integration time.

Therefore, when the difference between $Y_S$ and $Y_M$ is:

$$\Delta Y = Y_S - Y_M = K_1 \int_o^T \left[\log \left(\frac{E_{1S}}{E_{2S}} \cdot \frac{E_{2M}}{E_{1M}}\right)\right] dt \quad (10)$$

Next, assuming that the dyeing conditions and the values of the respective signals fluctuate as follows:

$$\begin{cases} E_{1M} \to k_1E_{1M} & E_{1S} \to k_1E_{1S} \\ E_{2M} \to k_2E_{2M} & E_{2S} \to k_2E_{2S}, \end{cases}$$

where $k_1$ and $k_2$ are fluctuation constants.

Then, rewriting equation (10):

$$\Delta Y = K_1 \int_o^T \left[\log \left(\frac{k_1E_{1S}}{k_2E_{2S}} \cdot \frac{k_2E_{2M}}{k_1E_{2S}}\right)\right] dt$$

$$= K_1 \int_o^T \left[\log \left(\frac{E_{1S}}{E_{2S}} \cdot \frac{E_{2M}}{E_{1M}}\right)\right] dt \quad (11)$$

As will be apparent upon comparing equation (10) with equation (11), the output $\Delta Y$ of the subtractor 19 is not affected even if the dyeing conditions fluctuate in the assumed manner.

The yarn to be measured and the standard yarn in this example must have experienced exactly the same dyeing conditions. Accordingly, the two yarns are usually dyed simultaneously.

The measuring means of this example may be used also, with certain changes, as the measuring means of the first example. For example, the measuring system S of standard yarn ($Y_S$) is severed so as to move only the measuring system M of the yarn to be measured ($Y_M$) and the output of the logarithmic calculator 16 may be introduced into the analogue recorder 17. Of course, the measuring system S of the standard yarn ($Y_S$) only may be used, contrary to the foregoing.

As will be apparent from the foregoing explanations, according to the present invention, upon measuring uniformity of the physical properties of yarn represented by the unevenness of its dye reception many remarkable functional effects occur, such as 1. knitting or weaving the yarn for visual checking is entirely unnecessary; measurements may be made on the yarn per se; they may be made promptly and the results may be fed back promptly to the quality control department, 2. because the measurement does not depend upon subjective human responses, there is no lack of uniformity due to individual differences, 3. by applying twist of at least 100 turns per meter to the yarn, accurate measurements may be carried out regardless of the type or shape of the yarn and independently of external elements such as noise, and 4. the dye unevenness of the yarn may be measured regardless of change of dyeing conditions as time goes by.

The following is claimed:

1. A process for measuring uniformity of the physical properties of a yarn to be tested, said yarn having a twist of at least about 100 turns per meter, which comprises the steps of:

1. applying to the running yarn a beam which has a spectrum that is continuous from the visible region to the near-infrared region, said beam being applied at such an angle that it is reflected from said yarn,
2. dividing said reflected beam into two,
3. imparting the characteristics of the near-infrared region to one of said divided beams,
4. imparting luminosity characteristics to the other of said divided beams, and
5. sensing the ratio of the intensity of said reflected beams.

2. In a process for producing yarn of improved uniformity, said process having a control parameter which affects said uniformity, the steps which comprise sensing said uniformity as a ratio in accordance with claim 1 and changing said parameter in response to changes of said ratio.

3. A process according to claim 1 wherein plural kinds of yarn are measured by interchanging them successively.

4. A process according to claim 1 further characterized by sensing the logarithm of said ratio.

5. A process according to claim 1 including the step of continuously dyeing said yarn to be measured and imparting a twist of at least about 100 turns per meter to said yarn.

6. A process for measuring non-uniformity of the physical properties of yarn which comprise the steps of 1. imparting a twist of at least about 100 turns per meter to the yarn to be measured and also to a standard yarn supplied continuously and simultaneously,
2. impinging upon both said yarns a beam whose spectrum is substantially continuous from the visible region of the near-infrared region,
3. impinging said beams so that they are reflected from said yarns,
4. dividing each of said reflected beams into two parts,
5. imparting characteristics of the near-infrared region to one of each of said divided parts,
6. imparting luminosity characteristics to the other of each of said divided parts,
7. sensing for each said yarn the ratio of the intensity of the beam having the characteristics of said near-infrared region to the intensity of the beam having said luminosity characteristics,
8. for each said yarn integrating said ratios during a predetermined period of time, and
9. subtracting the integrated value for said yarn to be measured from the integrated value for said standard yarn.

7. A process according to claim 6, further including the steps of simultaneously dyeing said yarns before the measurements are made.

8. An apparatus for measuring uniformity of the physical properties of yarn comprising:

1. means for continuously supplying yarn to be measured,
2. meams for winding said supplied yarn,
3. means between said yarn supplying means and said yarn winding means for imparting a twist of at least about 100 turns per meter to said yarn to be measured,
4. an incandescent lamp arranged for irradiating a beam to said twisted yarn,
5. a half mirror for dividing the beam reflected from said yarn into two reflected beams,
6. a near-infrared filter provided in the path of one divided beam of said reflected beam,
7. a luminosity filter provided in the path of the other divided beam of said reflected beam,
8. photoelectric converters arranged for converting the beams passing through said near-infrared and said luminosity filters to create electric signals for each, and
9. a calculator connected to receive said electrical signals for sensing the ratio of said electric signals.

9. Apparatus according to claim 8 including voltage amplifiers between said respective photoelectricity converters and said calculator.

10. Apparatus according to claim 8 wherein said calculator is arranged for sensing the logarithm of said ratio.

11. Apparatus for measuring uniformity of physical properties of yarn comprising:

1. means for supplying the yarn to be measured along with a standard yarn both being supplied continuously and silmultaneously,
2. means for winding both said yarns,
3. false twist means between said yarn supply means and said yarn winding means for imparting a twist of at least about 100 turns per meter to each of said yarns,
4. for each of said yarns
   - a. an incandescent lamp arranged for impinging a beam upon the twisted yarn so that the beam can be reflected from each yarn,
   - b. a half mirror for dividing the beam reflected from each said yarn into two parts,
   - c. a near-infrared filter provided in the path of one part of each said reflected beam,
   - d. a luminosity filter provided in the parth of each of the other parts of the reflected beam,
   - e. photoelectric converters for converting the beams passing through said near-infrared filter and through said luminosity filter into electric signals,
   - f. a calculator having means for sensing the ratio of the electric signals obtained by said respective photoelectric converters, and
   - g. integrators arranged for integrating each ratio obtained in (f), for a predetermined period of time, and
5. a subtractor connected to receive the output of each said integrator and having means for subtracting the output of said integrator for said yarn to be measured from the output of said integrator for said standard yarn.

12. An apparatus according to claim 11 comprising voltage amplifiers between the respective photoelectric converters and said calculator.

13. An apparatus according to claim 11, wherein said calculator includes means for sensing the logarithm of said ratio.

14. The apparatus according to claim 11, including means for changing a process parameter in the production of the yarn, and means responsive to the measured ratio connected to change said parameter.

* * * * *